(12) United States Patent
Birthisel et al.

(10) Patent No.: US 7,666,399 B2
(45) Date of Patent: Feb. 23, 2010

(54) PESTICIDAL FERTILIZER

(75) Inventors: Timothy D. Birthisel, Perrysburg, OH (US); Mark Weispape, Brenham, TX (US); Robin Smith, Austin, TX (US)

(73) Assignee: The Andersons, Inc., Maumee, OH (US)

( * ) Notice: Subject to any disclaimer, the term of this patent is extended or adjusted under 35 U.S.C. 154(b) by 79 days.

(21) Appl. No.: 11/301,171

(22) Filed: Dec. 12, 2005

(65) Prior Publication Data

US 2006/0142157 A1 Jun. 29, 2006

Related U.S. Application Data

(60) Provisional application No. 60/635,553, filed on Dec. 13, 2004.

(51) Int. Cl.
- *A01N 25/00* (2006.01)
- *A01N 25/08* (2006.01)
- *A01N 59/04* (2006.01)

(52) U.S. Cl. .......................... 424/84; 424/410; 504/101

(58) Field of Classification Search ................ 504/101; 424/84, 410
See application file for complete search history.

(56) References Cited

U.S. PATENT DOCUMENTS 5,006,361 A * 4/1991 Cox ............................ 426/601
5,518,517 A 5/1996 Jahnke et al.
6,479,062 B2 11/2002 Vander Hooven
2002/0173565 A1 * 11/2002 Blount ....................... 524/100

FOREIGN PATENT DOCUMENTS

| JP | 405221801 A | 8/1993 |
|----|-------------|--------|
| JP | 407109192 A | 4/1995 |
| JP | 02000313685 A | 11/2000 |
| JP | 02001048705 A | 2/2001 |

OTHER PUBLICATIONS

Azom.com, Particle Size—US Sieve Series and Tyler Mesh Size Equivalents, http://www.azom.com/details.asp?ArticleID=1417, Nov. 9, 2004.

* cited by examiner

*Primary Examiner*—Alton N Pryor
(74) *Attorney, Agent, or Firm*—Gifford, Krass, Sprinkle, Anderson & Citkowski, P.C.

(57) ABSTRACT

A composition is provided that includes in combination fertilizer particles inclusive of a plant nutrient component and a binder inhibitive of particle disintegration. The fertilizer particles are mixed with and dispersed in concert with bait particles attractive to a pest and inclusive of a pesticide or pest reproduction control agent. The bait particles remain sufficiently devoid of adherent fertilizer particle fragments so as to remain attractive to a target pest. Composition homogeneity is maintained by density matching between the fertilizer particles and bait particles or compensating for differences in density by sizing the lower density particles larger than the higher density particles.

23 Claims, 1 Drawing Sheet

PESTICIDAL FERTILIZER

RELATED APPLICATION

This application claims priority of U.S. Provisional Patent Application Ser. No. 60/635,553 filed Dec. 13, 2004, which is incorporated herein by reference.

FIELD OF THE INVENTION

The present invention relates in general to a combination delivering in concert fertilizer particles and bait particles having pesticidal or pest reproduction control agents therein and in particular to a composition for delivering in concert such that the bait particles are devoid of adherent fertilizer particulate fragments which tend to render the bait unattractive to a target pest.

BACKGROUND OF THE INVENTION

Crops, lawns, and other arrangements of useful or attractive vegetation require administration of fertilizer and pesticides in order to promote health of the plants concerned. In general, administration of these agents must be performed at regular intervals, making mechanical application of multiple agents desirable, since manual application is time consuming and expensive. However, simultaneous broadcast distribution of multiple agents is difficult where the agents are in different forms, such as a liquid pesticide and a solid fertilizer. Further, where multiple agents are present in a single form, the agents are preferably homogeneously distributed in a container for simultaneous broadcast distribution, in order to avoid unequal distribution to an area of crops, lawn or the like. One approach to homogeneous distribution of multiple agents is incorporation of the agents into a single particle. However, this approach is less suitable where it is desired to distribute a bait agent along with a fertilizer. Application of a bait agent is a technique used to attract a pest in order to induce the pest to ingest or otherwise be exposed to a pesticide or pest inhibitor. Inclusion of a fertilizer and a bait in a particle form may be disadvantageous where the fertilizer acts to repel the pest such that pest attraction to the bait is minimized and little or no pesticide is consumed. Further, some pests are likely to carry the bait away, for instance for communal ingestion. In that case, the fertilizer is likely to be moved away from a desired locus of action if combined in a single particle with a bait. Thus, there is a continuing need for a composition containing both a fertilizer and a pest bait wherein both the fertilizer and bait can be effectively evenly distributed, particularly over a large area, while maintaining effectiveness of both agents.

SUMMARY OF THE INVENTION

A composition is provided that includes in combination fertilizer particles inclusive of a plant nutrient component and a binder inhibitive of particle disintegration. The fertilizer particles are mixed with and dispersed in concert with bait particles attractive to a pest and inclusive of a pesticide or pest reproduction control agent. The bait particles remain sufficiently devoid of adherent fertilizer particle fragments so as to remain attractive to a target pest. Composition homogeneity is maintained by density matching between the fertilizer particles and bait particles or compensating for differences in density by sizing the lower density particles smaller than the higher density particles.

A bait particle particularly well suited for use in the composition includes as a total weight percent of the bait particles 40-70% carbohydrate, 5-20% protein, 10-20% fat, 5-20% water, 3-8% ash and 2-5% fiber along with an active pesticide or pest reproductive control agent. The resulting bait particle has a bulk density in the range of from 30-40 pounds per cubic foot. A fertilizer particle particularly well suited in such a composition includes a plant nutrient with the particles having a bulk density ranging from 45-80 pounds per cubic foot.

A method of promoting health of a target plant includes applying a composition as detailed above to the soil area proximate to a target plant. Such a composition is produced by coating the bait particles with an active agent and then blending the resultant bait particle coated with an active agent with fertilizer particles that incorporate a binder by way of a fluidizing blender to entrain air so as to inhibit transport of fertilizer particle fragments onto the bait particles. Particles containing fertilizer fragments are known to be less attractive to target pests, so retraining discrete bait particles and fertilizer particles within a simultaneous broadcast distribution of such a composition in the vicinity of a plant is of considerable importance.

DETAILED DESCRIPTION OF THE PREFERRED EMBODIMENTS

Figure 1:
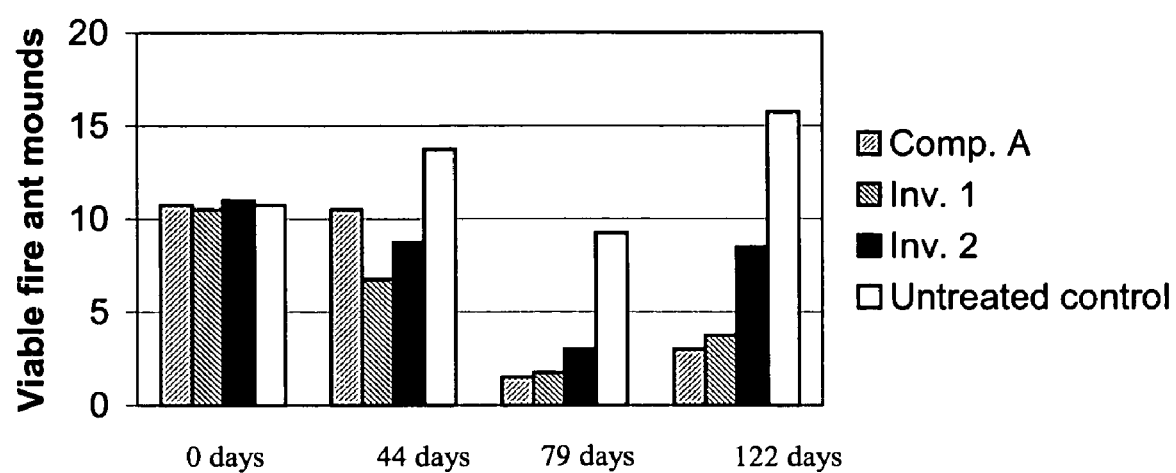
FIG. 1 is a plot of inventive composition control of fire ants compared to controls as a function of time.

The present invention has utility in promoting plant growth and inhibiting pests through simultaneous broadcast distribution of a composition containing bait particles and fertilizer particles. The present invention was facilitated by an appreciation that fertilizer particle fragments adhering to a bait particle render the bait particles unattractive to a target pest. Compositions and processes for practicing the present invention are disclosed hereinbelow.

A composition according to the invention includes two or more particle types, one or more including a fertilizer component and one including a pest bait component. The particles included in an inventive composition are capable of delivering a fertilizer or bait to a desired site without any significant adhesion of the fertilizer to the bait during production, distribution or application so as to retain the attractive aspects of the bait. The commingled fertilizer and bait particles included in a composition according to the invention are resistant to crushing and aggregation, and are generally free flowing. Crushing of fertilizer and bait particulate during mixing is inhibited through the use of a mechanical fluidizing blender to systematically entrain air into the mixture.

A preferred composition provided by the present invention includes a non-tacky bait particle, such that contact between the bait and fertilizer does not cause the bait particle to adhere a layer of fertilizer thereon, fertilizer tending to be repugnant to pests. An inventive composition is preferably produced by mixing two particle types as described herein. Optionally, more than two particle types are included in an inventive composition. For example, multiple bait particle types are included in one embodiment in order to attract multiple pest species.

A composition according to the invention includes a mixture of two or more particle types, each particle type having a bulk density. Particularly preferred is a composition in which fertilizer particle(s) and a bait particle are density matched. In general, particles are formulated to be density matched so as to favor maintenance of substantially homogeneous distribution of the two particle types in a container, such as during transport. Also, density matching serves to support homogeneous distribution of the two particle types during application, such as by broadcast distribution of the composition. The term "density matched" as used herein indicates that two particle types included in an inventive composition are formulated such that their bulk densities are within 70% of each other and preferably within 50% of each other.

Further included in the definition of the term "density matching" is a provision for size adjustment of one or both particle types. In one embodiment, where the bulk densities of the two particle type are not within 50% of each other, particle size is adjusted to provide a composition which resists separation of the two particle types, that is, for instance, movement of the heavier particle type to the bottom of a container with resulting displacement of the lighter particles and their concentration in the upper region of the container. Thus, in one embodiment, in a composition which includes a first particle which has a lower bulk density than a second particle, the size of the lighter particle type is decreased. In a preferred embodiment, the size of the lighter particle is decreased such that it has a volume in the range of 50-99.9% compared to the volume of the lighter particle.

In a particular example, a first particle has a bulk density of 20 lbs/ft$^3$ and a second particle has a bulk density of 50 lbs/ft$^3$. In order to provide an advantageous composition, the size of the second particle is decreased such that it has a volume in the range of 60-80% compared to the volume of the lighter particle.

A particularly advantageous composition includes fertilizer particle(s) and a bait particle which have substantially similar bulk densities. Preferably, both the fertilizer particle (s) and bait particle have a bulk density in the range of 2.5-80 lbs/ft$^3$, inclusive. More preferably, both the fertilizer particle (s) and bait particle each independently have a bulk density in the range of 20-60 lbs/ft$^3$, inclusive, and within 50% of each other. For example, in one embodiment, a first particle type has a bulk density in the range of 30 pounds per cubic foot—40 pounds per cubic foot, inclusive, and a second particle type has a bulk density in the range of 20 pounds per cubic foot—60 pounds per cubic foot, inclusive.

Typically, dimensionally averaged linear length of the particles is in the range of 0.0029 to 1 inch. In general, a preferred shape of particles included in an inventive composition is spherical or nearly spherical. However, other shapes may also be used illustratively including cylinders, rods, cones, discs, needles and irregular shapes. In one embodiment, the particles are preferably shaped to accommodate different types of spreaders, such as aerial spreaders and cyclone-type spreaders. Preferred shapes for such spreaders include spheres, generally flat oval platelets and pellets.

Fertilizer Particle

A fertilizer particle in an inventive composition includes a plant nutrient such as a macronutrient, secondary nutrient, micronutrient, nitrogen source, phosphorus source, potassium source, or combination thereof bioavailable in form initially or after decomposition to a plant. A bioavailable plant nutrient is in a form that fills a nutritional requirement of a plant either directly, where the plant is capable of physiological processing of an ingredient, or indirectly, where another organism such as a bacterium must first act on the ingredient to produce a form usable by the plant. Illustrative examples of a bioavailable nitrogen sources operative as plant nutrient ingredients include methylene urea oligomers and/or polymers, Nutralene, oxamide, urea formaldehyde-based compounds, dicyandiamide, crotilidiene diurea, nitrocellulose, metal ammonium phosphates, ammonium nitrate, ammonium sulfate, urea, coated urea, monoammonium phosphate, diammonium phosphate, calcium nitrate, isobutylidene diurea, urea-triazone, and other fertilizers as detailed herein. NPK sources operative herein as single or multiple sources of nitrogen, phosphorus, and/or potassium include: ammonium phosphate, triple super phosphate, phosphoric acid, potassium sulphate, potassium nitrate, potassium metaphosphate, potassium chloride, dipotassium carbonate, potassium oxide and a combination thereof.

In one embodiment of a fertilizer particle included in an inventive composition, a nitrogen source is present in an amount ranging from 30% to 99.5% by weight of the total dry weight of the fertilizer particle. In a further embodiment, the nitrogen source is present in an amount ranging from 50% to 99% by weight of the total dry weight of the fertilizer particle.

Preferably, included in a fertilizer particle is a binder component present in an amount ranging from 5% to 75% by weight of the total dry weight of the fertilizer particle. In a further embodiment, the binder component is present in an amount ranging from 1% to 25% by weight of the total dry weight of the fertilizer particle. A binder component is included in a fertilizer particle as necessary to produce or promote cohesion in forming a particle capable of retaining a specified form during transport and/or distribution. A binder component may be a carbohydrate, protein, lipid, synthetic polymer, glycolipid, glycoprotein, lipoprotein, lignin, a lignin derivative, a carbohydrate-based composition, and a combination thereof. In a preferred embodiment the binder component is a lignin derivative and is optionally calcium lignosulfonate. In another option, the binder component is selected from the group consisting of: a monosaccharide, a disaccharide, an oligosaccharide, a polysaccharide and combinations thereof. Specific carbohydrate binders illustratively include glucose, mannose, fructose, galactose, sucrose, lactose, maltose, xylose, arabinose, trehalose and mixtures thereof such as corn syrup; celluloses such as carboxymethylcellulose, ethylcellulose, hydroxyethylcellulose, hydroxymethylethylcellulose, hydroxyethylpropylcellulose, methylhydroxyethyl-cellulose, methylcellulose; starches such as amylose, seagel, starch acetates, starch hydroxyethyl ethers, ionic starches, long-chain alkyl starches, dextrins, amine starches, phosphates starches, and dialdehyde starches; plant starches such as corn starch and potato starch; other carbohydrates such as pectin, amylopectin, xylan, glycogen, agar, alginic acid, phycocolloids, chitin, gum arabic, guar gum, gum karaya, gum tragacanth and locust bean gum; vegetable oils such as corn, soybean, peanut, canola, olive and cotton seed; complex organic substances such as lignin and nitrolignin; derivatives of lignin such as lignosulfonate salts illustratively including calcium lignosulfonate and sodium lignosulfonate and complex carbohydrate-based compositions containing organic and inorganic ingredients such as molasses. Suitable protein binders illustratively include soy extract, zein, protamine, collagen, and casein. Binders operative herein also include synthetic organic polymers capable of promoting or producing cohesion of particle components and such binders illustratively include ethylene oxide polymers, polyacrylamides, polyacrylates, polyvinyl pyrrolidone, polyethylene glycol, polyvinyl alcohol, polyvinylmethyl ether, polyvinyl acrylates, polylactic acid, and latex. In a preferred embodiment, the binder is calcium lignosulfonate, molasses, a liquid corn starch, a liquid corn syrup or a combination thereof.

A fertilizer component optionally includes an active ingredient such as a soil nutrient, an amendment material, a biostimulant, and a combination thereof. An active ingredient is typically present in an amount ranging from 0.05% to 50% by weight of the total dry weight of the particle. In a more preferred embodiment, the soil nutrient, amendment material, or biostimulant is present in an amount ranging from 0.1% to 30% by weight of the total dry weight of the particle. In a still more preferred embodiment, the soil nutrient, amendment or biostimulant is present in an amount ranging from 0.5% to 10% by weight of the total dry weight of the particle.

Exemplary soil nutrients include calcium, magnesium, sulfur, iron, manganese, copper, zinc; oxides thereof; salts thereof, and a combination thereof.

Exemplary amendment materials include humic acid, blood meal, bone meal, seed meal, feather meal, soy meal, meat meal, animal waste, activated sludge, hydrolyzed animal hair, a fish byproduct, chitin, composts and a combination thereof. In addition, a fertilizer particle optionally includes an additive to aid in particle formation illustratively including an anti-dust agent, an anti-caking agent, a filler, a preservative, and a combination thereof.

A biological factor or biostimulant is optionally included as an active ingredient in an amount ranging from 0.05% to 10% by weight of the total dry weight of the particle. In a more preferred embodiment, the biological factor or biostimulant active ingredient is present in an amount ranging from 0.1% to 5% by weight of the total dry weight of the particle. In a still more preferred embodiment, the biological factor or biostimulant active ingredient is present in an amount ranging from 0.25% to 1% by weight of the total dry weight of the particle.

Biostimulants are substances that promote plant survival and health and illustratively include plant growth hormones and plant growth regulators such as cytokinins, auxins, gibberellins, ethylene, absisic acid and a combination of these.

A fertilizer particle is formed by a process such as mechanical agglomeration, for instance as described in examples below.

Bait Particle

A bait particle included in an inventive composition includes a nutritive component attractive to a target undesirable organism. In a preferred embodiment, the nutritive component includes food waste, such as bakery waste, confectionery waste, snack waste and cereal waste, either alone or in combination with one another, as a bait carrier for pesticide chemicals. Bakery waste is a mixture of bakery products such as bread, cookies, cakes, crackers, flours and doughs which have been mechanically separated from non-edible material, artificially dried and ground. Confectionery waste is a mixture of confectionery products such as candy bars, hard candy, jelly beans, chocolates, chocolate syrup and flavored syrups that have been separated from non-edible material, artificially dried and ground. Snack waste is a mixture of snack food products such as potato chips, pretzels, corn chips, popcorn, caramel corn and cheese curls that have been separated from non-edible material, artificially dried and ground. Cereal waste is a mixture of cereal products such as wheat flakes, corn flakes, puffed rice, shaped oats, shredded wheat, oatmeal and rolled oats separated from non-edible material, artificially dried and ground. While the particles are usually composed of bakery, confectionery, snack and cereal wastes as ingredients to the overall final product, original food ingredients may be used to simulate such wastes. The mixture of original food ingredients may be prepared and processed the same as described above with respect to use of the wastes.

In preparation for inclusion in a bait particle, the food waste product is crushed, ground and reduced in size to where the majority of the particles pass through a 6 mesh screen and passes over a 100 mesh screen (U.S. Standard Sieve Series). The over 6 mesh screen particles are returned to the initial grinding process until the desired particle size is obtained or may be reconstituted to pass through the 6 mesh screen and over the 100 mesh screen. The preferred particle size is between a 10 mesh (pass through) and a 40 mesh (pass over). The resulting preferred product which passes through a 10 mesh screen and over a 40 mesh screen (−10+40) is controlled to have a bulk density between 6 and 40 pounds per cubic foot, with a density between 30 and 40 pounds per cubic foot being preferred.

Typically, the food waste includes a carbohydrate, a protein, a fat, a liquid, and a combination thereof. In some bait particles included in a composition according to the present invention, fats and oils such as soybean oil will be added to the processed waste product particles as a vehicle to carry the pesticide and to act as an added attractant to the pest. The particles have the ability to absorb up to 20% soybean oil and still remain flowable for easy field applications using spreaders, hand application or aerial application. Preferably, not more than 5% soybean oil is added to the processed waste particles, if needed. Other examples of fats and oils that can be used include vegetable oils, pine oils and animal fats.

In one embodiment, the food waste includes a carbohydrate in an amount ranging from 40-70 percent by weight, inclusive; a protein in an amount ranging from 5-20 percent by weight, inclusive; a fat in an amount ranging from 10-20 percent by weight, inclusive; and water in an amount ranging from 5-20 percent by weight, inclusive. Optionally, a bait particle includes a further component illustratively including a filler, a coloring agent, a sweetener, a binder, a wood product, an anti-caking agent, an anti-dust agent and an antioxidant. The processed particles are often dyed to a predetermined color. This aids the identification of different end use products with no adverse effects. Further optionally, the bait particle includes ash and/or fiber such as ash in an amount ranging from 3 to 8 percent by weight, inclusive and/or fiber in an amount ranging from 2 to 5 percent by weight, inclusive.

Edible granules are conventional to the art that include a methylene urea coating resulting in a non-tacky particle. These conventional bait particles lack a pesticide or pest reproductive control active agent. To a methylene urea coated conventional edible granule, an additional coating is added containing a pesticide or pest reproductive control active agent. Typically, the pesticide or pest reproductive control active agent is added to a binder solution as detailed with respect to the fertilizer particle and applied to the granule. Upon drying of the pesticide or pest reproductive control active agent and binder on the granule, an inventive bait particle is obtained.

A bait particle further includes a pesticide for killing or inhibiting infestation by a target pest organism includes an arachnid; a bacterium; a bird; a fungus; an insect; a mammal, such as a rodent; a virus; and a worm. The pesticide is typically present from 0.001 to 2 total weight percent of the bait particle.

A pesticide includes such agents as an acaracide, an antimicrobial, a bactericide, an entomopathogen, a fungicide, an herbicide, an insecticide, a molluscicide, a nemacide (or nematocide,) a rodenticide, a pheromone, a chemosterilant, a viricide, an imagocide, a larvicide, an ovicide, a formicide, an aphidicide, a muscacide, a culicicide, an anophelicide, an arachnidcide, and a vespacide. Preferably, an inventive bait particle containing a toxic invertebrate pesticide also contains a mammalian and/or avian ingestion repellant. More preferably, it also contains both mammalian and avian ingestion repellants to lessen the likelihood of incidental ingestion by bystander higher species. Mammalian ingestion repellants illustratively include cadaverine, butyric acid, and capsacin. Avian repellants include artificial grape flavorant.

A pest reproductive control agent operative herein includes a pheromone, molting signaling compound or steroid that upon contact with the target pest decreases the reproductive capacity of the pest. A pest reproductive control agent is preferred over a pesticide since a reproductive control agent is specific to a species or narrower group of organisms, does not bioaccumulate, and is less detrimental to predatory or bystander organisms in the pest habitat. Additionally, a reproductive control agent is unlikely to avoid the bait due to ill health effects associated with sampling, as is often the case with a lethal pesticide. A pest reproductive control agent is typically present from 0.0001 to 1 total weight percent of the bait particle.

In some embodiments a solvent may be included in a bait particle, for instance in conjunction with solvation of a component such as a pest inhibiting agent. For instance, a solvent such as water, acetone, ethanol and the like may be used in order to facilitate inclusion of an ingredient in a bait particle. In general, an organic solvent may be evaporated following inclusion in a bait particle and has no adverse effects on the bait particle's attractiveness to the target pest.

Optionally, a bait particle included in a composition according to the present invention includes a preservative to prolong shelf and field life. In addition, a preservative may be included as an aid in retarding the loss of oil when the bait particles are spread on hot concrete or soil.

Further optionally included ingredients include flavoring or nutritive additives such as sugar, molasses and wood flour. In a particular embodiment, such components may be included in a bait particle in addition to those described above. Generally, such additives are included in an amount ranging between 1% to 12%, inclusive by weight of the total bait particle composition. For example, sugar broadens the olfactory range and is optionally added in an amount in the range of 1% to 7% by weight, inclusive, of the total bait particle composition. Molasses is optionally included as an additive in an amount in the range of 3% to 12% by weight, inclusive, of the total bait particle composition. In a further option, a nutritive additive such as wood flour is added in an amount in the range of 1% to 10% by weight, inclusive, of the total bait particle composition, for instance to encourage ingestion by wood eating insects.

In general, a bait particle included in an inventive composition is resistant to rainfall and high humidity when used in open areas. However, a water-repellent binder is optionally included to increase resistance to high moisture conditions without harming its attractiveness to a target pest. In one embodiment, a water-repellant binder is added in an amount in the range of 4% to 15% by weight, inclusive, of the total bait particle composition.

Typically, a bait particle formulated as described above is free flowing. However, in some embodiments an anti-caking agent is optionally added to reduce the tendency of individual particles to adhere to one another without harming the attractiveness of the bait particle to the target pest. In one embodiment, an anti-caking additive is added in an amount in the range of 4% to 10% by weight, inclusive, of the total bait particle composition.

A bait particle as described above generally has inherent preservative characteristics which inhibit mold at moistures not above 14%. However, an antioxidant is optionally added to prolong the shelf and/or field life of a bait particle included in an inventive composition. Antioxidants protect against deterioration of the bait particle caused by oxidation, such as fat rancidity and color changes, without interfering with the attractiveness of the bait particle to a target pest. In a particular embodiment, an antioxidant is added in an amount up to 0.5% by weight of the total bait particle composition.

Methods

A method of promoting health of a target plant is provided by the present invention. An inventive method includes the step of applying an inventive composition as described herein to an area proximate to a target desirable plant. Application of the composition fertilizes the target plant by supplying bioavailable nitrogen and other optional ingredients. Further, delivery of the inventive composition attracts one or more target pests and inhibits infestation of the plant and the area proximate to the target plant by a pest by stimulating consumption of bait and thereby bringing the pest into contact with a pesticide or other pest inhibitor. The health of the target plant is promoted both by fertilization and by inhibition of pest infestation.

In another an inventive method for promoting a desired environment in a specified region is provided. Such a method includes the step of providing a composition having a fertilizer particle and a bait particle as described herein and applying the composition to the specified region in which the desired environment is to be promoted. For example, a specified region may include an area such as a golf course, park, lawn or the like wherein one or more desirable target plants, such as particular types of grasses, trees or shrubs are to be encouraged. In the same specified region it may be desirable to inhibit a target pest. For example, it may be desirable to discourage infestation and/or feeding by the pest in the specified region in order to limit harmful or unwanted effects of pest presence such as plant destruction, tunneling, disease, and the like. Application of an inventive composition stimulates growth of a target plant by fertilization. Further, application of an inventive composition acts to inhibit infestation and other activity by a target pest by delivering a pest attractive bait and subsequent ingestion or other contact with a pesticide. Thus, application of an inventive composition promotes a desired environment in a specified region.

EXAMPLES

Example 1

Bait Particle Formulation

A bait particle is formulated which includes: water: 7.5% by weight of the total bait particle; protein: 11.3% by weight of the total bait particle; fiber: 2.0% by weight of the total bait particle; ash: 3.5% by weight of the total bait particle; fat (oil): 11.2% by weight of the total bait particle; and carbohydrate: 64.5% by weight of the total bait particle. Bait particles were formed which had a size from about 6 mesh to about 50 mesh (−6+50), U.S. Standard Sieve Series, and a density of about 35 pounds per cubic foot.

Example 2

Exemplary Particle Preparation

Using a pan agglomeration disk, particle ingredients are combined and mixed. The agglomeration disk is operated and adjusted to generate the desired size distribution of particles before the particles are conveyed to a fluid bed dryer where the material was dried at a temperature of 140° F. to a moisture content of less that 0.5%. The material is then separated into various size categories using conventional gyroscopic screeners. The range of sizing for each product stream can be varied to separate the desired material from the mixture of sizing.

Example 3

Post-production Surface Coating of a Fertilizer Particle or a Bait Particle

Particles are fed to a blender (such as a Forberg fluidized zone blender) or other coating equipment (such as a coating drum). The material is sprayed with a methylene urea, containing in the case of the bait particle, a 0.3% by weight of the solution of methyl parathion and the coating is allowed to dry to a hard dry coating. The fertilizer and bait particles are mixed at an 8:1 weight ratio with a mechanical fluidizing blender for 30 minutes to achieve a homogenous mixture nearly devoid of broken particulate.

Example 4

Determination of Resistance to Attrition

Apparatus: Ro-Tap sieve shaker with 8-inch sieves, balance with 0.1 g sensitivity, 10-min. timer, and 10 steel balls with smooth surfaces and 16 mm (⅝ in.) in diameter.
1. Using information from the Screen Analysis, choose your limiting screen size.
2. Place about 75 g of a representative sample onto the limiting screen.
3. Reassemble the screen apparatus with the limiting screen just above the pan.
4. Place the screen apparatus onto the shaker and run it for 10 min. (use the hammer).
5. Empty the pan. Transfer 50.0 g of sample to the pan.
6. Put ten (10) 16-mm steel balls in the pan with the sample.
7. Reassemble the screen apparatus and place it onto the shaker and run it for 10 min. (do not use the hammer).
8. Remove the steel balls from the pan and transfer the sample back into the limiting screen.
9. Place the screen apparatus back onto the shaker and run it for 10 min. (use the hammer).
10. Weigh out the amount that remained on the limiting screen to the nearest 0.1 g and compare it to the original amount.

Percent resistance to attrition=$\{(100 \cdot a)/b\}$, where a is the weight of the fraction that remained on the limiting screen in Step 10 and b is total weight of the sample in Step 5. The particles of the present invention have an exemplary minimum Resistance To Attrition (RTA) rating ranging from 60% to 100%.

Example 5

Evaluation of Inventive Composition Efficiency Compared to Conventional Bait for Control of Red Fire Ants A bait particle formulation having an average mesh size of 6 is loaded to 0.5 total weight percent with application of a pyriproxyfen containing soybean oil solution (comparative Example A). The bait particles have a bulk density of 25 pounds per cubic foot. The pyriproxyfen coated bait particle is then mixed with fertilizer particles containing a 14-0-27 nitrogen-phosphorus-potassium content. The fertilizer particles have a bulk density of 48 pounds per cubic foot and an average particle size of between 0.11 and 0.13 inches (corresponding to −6+7 mesh). The bait particles and fertilizer particles are mixed such that the bait particles make up 0.85 weight percent of the mixture with mixing occurring in a mechanical fluidized blender. One fertilizer particle sample is completely coated with calcium lignosulfonate to a level of 10% by weight of the total dry weight of the fertilizer particle (inventive Composition 1, abbreviated Inv. 1). The coated fertilizer particles are then mixed with an equal weight amount of uncoated fertilizer particles and then combined with the bait particles to a loading of 0.85 weight percent bait particles of Comparative Example A (inventive Composition 2, abbreviated Inv. 2).

A trial was performed commencing on Jun. 21, 2005 on grounds surrounding an office complex in Fayetteville, N.C. Tests plots were established along streets and fence lines to include at least ten fire ant mounds per plot. A comparative or inventive composition was uniformly spread throughout a test plot. The soil surface was dry at application with no rain occurring for the next 48 hours. The grass on the test plots was mowed every two weeks for the duration of the test. In addition to comparative Example A and inventive Compositions 1 and 2, an untreated control set of plots was established with four replicates of each type of treatment plot being established. The counts for the four replicates of each treatment were averaged to obtain statistically meaningful data as to the total number of viable fire ant mounds.

Comparative Composition A was treated with 1.5 pounds of bait particles per acre while inventive composition plots were treated 1.5 pounds of bait particles and 174 pounds of fertilizer particles per acre.

The results as to the number of fire ant mounds were measured at 0, 44, 79 and 122 days after treatment. The results are summarized in FIG. 1.

Any patents or publications mentioned in this specification are incorporated herein by reference to the same extent as if each individual publication was specifically and individually indicated to be incorporated by reference. In particular, U.S. Pat. No. 6,479,062 is incorporated herein by reference.

One skilled in the art will readily appreciate that the present invention is well adapted to carry out the objects and obtain the ends and advantages mentioned, as well as those inherent therein. The inventions described herein are presently representative of preferred embodiments. Thus, they are exemplary and are not intended as limitations on the scope of the invention or inventions. Changes therein and other uses will occur to those skilled in the art. Such changes and other uses are encompassed within the spirit of the invention as defined by the scope of the claims.

The invention claimed is:

1. A composition comprising in combination:
    a plurality of fertilizer particles having a fertilizer average size, each of said plurality of fertilizer particles comprising a plant nutrient component and a binder inhibitive of disintegration; and
    a plurality of bait particles having an average bait particle size comprising an active agent selected from the group consisting of: a pesticide and pest reproduction control agent, said plurality of bait particles produced such that following mixing with said plurality of fertilizer particles, said plurality of bait particles are devoid of adherent fertilizer particle fragments so as to remain attractive to a target pest.

2. The composition of claim 1 wherein said plant nutrient is selected from die group consisting of a macronutrient, a secondary nutrient, a micronutrient, a nitrogen source, a phosphorus source, and a potassium source.

3. The composition of claim 1 wherein said plurality of fertilizer particles further comprises at least one component consisting of a soil nutrient, an amendment material, and a biostimulant.

4. The composition of claim 2 wherein said component is present in an amount ranging from 30% to 99.5% by weight of the total dry weight of the fertilizer particle.

5. The composition of claim 2 wherein said plant nutrient and said nitrogen source is selected from the group consisting of: a methylene urea polymer, oxamide, dicyanamide, crotilidiene diurea, nitrocellulose, metal ammonium phosphates, ammonium nitrate, ammonium sulfate, Nutralene, urea, coated urea, monoammonium phosphate, diammonium phosphate, calcium nitrate and isobutylidene diurea, and urea-triazone, and a combination thereof.

6. The composition of claim 4 wherein the a binder within said plurality of fertilizer particles present in an amount ranging from 5 to 75 total weight of said plurality of fertilizer particles.

7. The composition of claim 6 wherein the binder is selected from the group consisting of: a monosaccharide, a disaccharide, an oligosaccharide, a polysaccharide and combinations thereof.

8. The composition of claim 1 wherein the active agent is selected from the group consisting of: an herbicide and a fungicide.

9. The composition of claim 1 wherein said plurality of bait particles comprise a nutritive component attractive to a pest.

10. The composition of claim 9 wherein the nutritive component comprises food waste.

11. The composition of claim 10 wherein the food waste comprises a component selected from the group consisting of: a carbohydrate, and a protein, a fat, and a combination thereof.

12. The composition of claim 11 wherein the food waste comprises the carbohydrate in an amount ranging from 40-70 total weight percent; the protein in an amount ranging from 5-20 total weight percent; the fat in an amount ranging from 10-20 total weight percent; and water in an amount ranging from 5-20 total weight percent of said plurality of bait particles.

13. The composition of claim 1 wherein the pesticide or pest reproduction control agent is selected from the group consisting of: an acaracide, an antinticrobial, a bactericide, an entomopathogen, a fungicide, an herbicide, an insecticide, a nemacide, a rodenficide, a pheromone, a chemosterilant, a viricide, an insect growth regulator, an imagocide, a larvicide, an ovicide, a forunicide, an aphidicide, a muscacide, a culicicide, an anophelicide, an arachnidcide, and a vespacide.

14. A process of promoting a desired environment in a specified region, comprising:
providing a composition according to claim 1; and
applying the composition to the specified region, such that the composition stimulates growth of a target plant and inhibits a target pest such that the desired environment in the specified region is promoted.

15. A composition comprising in combination:
a plurality of fertilizer particles having a fertilizer average size, each of said plurality of fertilizer particles comprising a plant nutrient component and a binder inhibitive of disintegration; and
a plurality of bait particles having an average bait particle size comprising an active agent selected from the group consisting of: a pesticide and pest reproduction control agent, said plurality of bait particles produced such that following mixing with said plurality of fertilizer particles, said plurality of bait particles are devoid of adherent fertilizer particle fragments so as to remain attractive to a target pest;
wherein said plurality of fertilizer particles have a first bulk density, said plurality of bait particles have a second bulk density, and the first and second bulk densities are within 50% of one another.

16. The composition of claim 15 wherein when the first bulk density is greater than the second bulk density, the fertilizer average size is less than the average bait particle size.

17. The composition of claim 15 wherein said plurality of bait particles and said plurality of fertilizer particles each independently has a bulk density in the range of 2.5-80 lbs/ft$^3$.

18. The composition of claim 16 wherein the average bait particle size and the average fertilizer particle size are each independently in the range of 0.0029 to 1 inch in diameter.

19. A composition comprising in combination:
a plurality of fertilizer particles having a fertilizer average size, each of said plurality of fertilizer particles comprising a plant nutrient component and a binder inhibitive of disintegration; and
a plurality of bait particles having an average bait particle size comprising an active agent selected from the group consisting of: a pesticide and pest reproduction control agent said plurality of bait particles produced such that following mixing with said plurality of fertilizer particles, said plurality of bait particles are devoid of adherent fertilizer particle fragments so as to remain attractive to a target pest;
wherein said plurality of bait particles further comprise ash in an amount ranging from 3 to 8 total weight percent of said plurality of bait particles.

20. A composition comprising in combination:
a plurality of fertilizer particles having a fertilizer average size, each of said plurality of fertilizer particles comprising a plant nutrient component and a binder inhibitive of disintegration; and
a plurality of bait particles having an average bait particle size comprising an active agent selected from the group consisting of: a pesticide and pest reproduction control agent, said plurality of bait particles produced such that following mixing with said plurality of fertilizer particles, said plurality of bait particles are devoid of adherent fertilizer particle fragments so as to remain attractive to a target pest;
wherein said plurality of bait particles further comprise fiber in an amount ranging from 2 to 5 total weight percent of said plurality of bait particles.

21. A composition comprising in combination:
a plurality of fertilizer particles having a fertilizer average size, each of said plurality of fertilizer particles comprising a plant nutrient component and a binder inhibitive of disintegration; and
a plurality of bait particles having an average bait particle size comprising an active agent selected from the group consisting of: a pesticide and pest reproduction control agent, said plurality of bait particles produced such that following mixing with said plurality of fertilizer particles, said plurality of bait particles are devoid of adherent fertilizer particle fragments so as to remain attractive to a target pest;
wherein said plurality of bait particles comprise on a total weight percent of said plurality of bait particles from 40% to 70% carbohydrates; 5% to 20% protein; 10% to 20% fat; 5% to 20% water; 3% to 8% ash; and 2% to 5% fiber, the average bait particle size in the range from −6 to −50, U.S. Standard Sieve Series, and the bulk density in the range from 30 pounds per cubic foot to 40 pounds per cubic foot.

22. A composition comprising:

a plurality of bait particles comprising at a total weight percent of said plurality of bait particles 40% to 70% carbohydrate, 5% to 20% protein, 10% to 20% fat, 5% to 20% water, 3% to 8% ash, 2% to 5% fiber, and an active pesticide or pest reproductive control agent, said plurality of bait particles having a bulk density in the range from 30 pounds per cubic foot to 40 pounds per cubic foot, said plurality of bait particles devoid of adherent fertilizer particle fragments so as to remain attractive to a target pest; and a plurality of fertilizer particles comprising a plant nutrient component, said plurality of fertilizer particles having a bulk density in the range of 45 pounds per cubic foot to 80 pounds per cubic foot.

23. The composition of claim 22 wherein said plurality of bait particles and said plurality of fertilizer particles each independently has an average size in the range of −6 to −50, U.S. Standard Sieve Series.

\* \* \* \* \*